United States Patent [19]

Duranleau et al.

[11] 4,000,194

[45] Dec. 28, 1976

[54] PREPARATION OF ALKYLAMIDES

[75] Inventors: Roger D. Duranleau, Ardonia; John M. Larkin, Wappingers Falls, both of N.Y.

[73] Assignee: Texaco Inc., New York, N.Y.

[22] Filed: Jan. 8, 1976

[21] Appl. No.: 647,400

[52] U.S. Cl. .................. 260/561 R; 260/566 D
[51] Int. Cl.² ................................. C07C 103/127
[58] Field of Search ................. 260/561 R, 566 D

[56] References Cited

UNITED STATES PATENTS

| | | | |
|---|---|---|---|
| 2,640,846 | 6/1953 | Hurwitz et al. | 260/561 R |
| 3,274,170 | 9/1966 | Ugi et al. | 260/561 R |
| 3,929,845 | 12/1975 | Duranleau et al. | 260/561 R |

*Primary Examiner*—Arthur P. Demers
*Attorney, Agent, or Firm*—T. H. Whaley; C. G. Ries; George J. Darsa

[57] ABSTRACT

Alkylamides are prepared by heating an acylhydroximyl halide in an oxygenated polar organic solvent at a temperature of about 70° to 190° C. The alkylamides herein prepared are useful as fuel and lubricant additives and as intermediates in the preparation of acids, nitriles and amines.

23 Claims, No Drawings

PREPARATION OF ALKYLAMIDES

BACKGROUND OF THE INVENTION

This invention relates to a novel method of preparing alkylamides. In particular, this invention relates to a method for preparing alkylamides from acylhydroximyl halides.

Alkylamides can be prepared by the amination of carboxylic acids. However, many carboxylic acids are not readily available, particularly the odd carbon number chain fatty acids. Illustratively, the acids can be produced by oxidizing the corresponding alcohol or by employing a Grignard synthesis, each however requiring costly starting materials. Other methods for preparing alkylamides include the conversion of nitro-nitrosoalkane dimers by reaction with at least molar amounts of an anhydrous mineral acid for relatively short contact times. This method is not attractive inasmuch as the mineral acid is consumed in the course of the reaction and the concentration of the charge in the strong acid must be kept low to avoid explosive reactions. The reaction is also water sensitive and the presence of water causes the alkylamides to be hydrolyzed to acids. Further, the amount of concentrated acid employed requires the use of costly corrosion resistant equipment. A method has now been found whereby a range of individual or mixtures of alkylamides having from 2 to 51 carbon atoms can be produced in good yields and where the method can be conducted in less costly equipment.

SUMMARY OF THE INVENTION

Broadly, this invention contemplates a method of preparing an alkylamide which comprises heating an acylhydroximyl halide in an oxygenated polar organic solvent at a temperature of about 70° to 190° C. The method produces as by-products carbon dioxide and a hydrogen halide.

According to this invention, the contemplated alkylamides are prepared from acylhydroximyl halides corresponding to the formula:

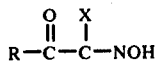

where R is an alkyl group having from 1 to 50 carbon atoms, suitably from 3 to 40 carbons and preferably 5 to 30 carbons, and where X is Cl, Br, I or F. Included as starting materials we mention, acetylhydroximyl chloride, acetylhydroximyl bromide, acetylhydroximyl iodide, acetylhydroximyl fluoride, propionylhydroximyl chloride, butanoylhydroximyl chloride, pentanoylhydroximyl chloride, pentanoylhydroximyl bromide, pentanoylhydroximyl iodide, pentanoylhydroximyl fluoride, hexanoylhydroximyl chloride, nonanoylhydroximyl chloride, undecanoylhydroximyl chloride, undecanoylhydroximyl bromide, undecanoylhydroximyl iodide, undecanoylhydroximyl fluoride, tetradecanoylhydroximyl chloride, pentadecanoylhydroximyl chloride, pentadecanoylhydroximyl bromide, pentadecanoylhydroximyl iodide, pentadecanoylhydroximyl fluoride, heptadecanoylhydroximyl chloride and eicosanoylhydroximyl chloride. Mixtures of acylhydroximyl halides as starting material are also contemplated and are converted to individual amides or to mixtures of amides depending upon whether in the starting reactant R represents a uniform alkyl group or a range or mixture of alkyl groups. The acylhydroximyl halides contemplated as reactants herein can be prepared by the procedure described in our copending application Ser. No. 532,421, filed December 12, 1974, which is herein incorporated by reference. Essentially the procedure in our copending application involves contacting a 1-nitro-2-alkanone having from 3 to 52 carbon atoms with a halogen acid, such as hydrochloric acid, hydrobromic acid, hydroiodic acid or hydrofluoric acid, in the presence of a polar protic organic solvent, such as a carboxylic acid or alcohol having 2 to 16 carbons illustrated by acetic acid, hexanoic acid, ethanol and butanol, at from about 50° to 105° C. where the mole ratio of nitroketone to halogen acid to solvent is about 1:1:1 and 1:30:100. Recovery of the acylhydroximyl halide product can be accomplished by cooling the reaction mixture to below about 30° C. and collecting the crystallized solids.

The method contemplated by this invention provides as the desired product an alkylamide of the formula:

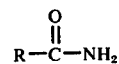

where by-products of the method are a hydrogen halide (HX) and carbon dioxide ($CO_2$) and where R and X are as heretofore defined. The alkylamide formed by the method possesses one carbon less than the starting acylhydroximyl halide and the conversion reaction involves transformation of the halide through rearrangement and cleavage.

More specifically, the method of this invention involves heating an acylhydroximyl halide of the formula above or mixtures thereof in the presence of an oxygenated polar organic solvent at a temperature of about 70° C and up to about 190° C., suitably from 90° to 140° C. and preferably from 110° to 140° C. At reaction temperatures below 70° C. substantially no formation of alkylamides occurs. Reaction temperatures exceeding 190° C. cause a substantial reduction in the formation of the desired alkylamide and instead acid formation is promoted.

In accordance with our method, the acylhydroximyl halide is contacted with an oxygenated polar organic solvent employing mole ratios of acylhydroximyl halide to solvent of between about 1:1 and 1:100, preferably between 1:4 and 1:40. At the reaction temperature specified above the reaction time is suitably between about one-quarter and 24 hours or longer. Further, the solvent employed should be sufficiently polar to permit the rearrangement reaction to occur and is further characterized as being capable of solubilizing the acylhydroximyl halide reactant, water and hydrogen halide by-product. Essentially no reaction will occur when non-polar solvents, such as benzene, hexane, toluene or non-oxygenated polar solvents such as methylene chloride, chloroform or 1,2-dichlorobenzene are employed.

The contemplated oxygenated polar organic solvents employed herein are illustrated by alkanoic acids, alkylformamides, alkylacetamides, alkylsulfoxides, alkylureas, alkylphosphoramides, alkylpyrrolidinones, aldehydes, ketones and ethers.

Specific examples of the solvents employed in the instant method are dimethylformamide, diethylformamide, dimethylacetamide, dimethylsulfoxide, diethylsulfoxide, tetramethylurea, tetraethylurea, hexamethylphosphoramide, 1-methyl-2-pyrrolidinone, 1-ethyl-2-pyrrolidinone, 1,4-dimethyl-2-pyrrolidinone, butyraldehyde, acetone, methylethylketone, diethylether, 1,4-dioxane, tetrahydrofuran and tetrahydropyran. Mixtures of oxygenated polar solvents can also be used. A preferred oxygenated polar solvent is dimethylsulfoxide. In general, any oxygenated polar organic solvent characterized above that is a liquid under the processing conditions set forth herein can be employed.

As highly preferred solvents in our method we mention alkanoic acids having 1 to 16 carbon atoms, particularly those of 2 to 6 carbons, including formic acid, acetic acid, propionic acid, butanoic acid, isobutanoic acid, pentanoic acid, hexanoic acid, octanoic acid, decanoic acid, undecanoic acid, dodecanoic acid and hexadecanoic acid.

While the method described herein does not contemplate water as a reaction solvent, some water is essential as a reactant in the rearrangement and cleavage reaction. In general, from about one mole to below about five moles, preferably 2 to 4 moles, of water are employed in the method per mole of acylhydroximyl halide. The lower mole ratios of water are generally utilized at the higher reaction temperatures. Under the conditions described herein, hydrolysis is controlled and the alkylamide is provided in good yields as will be understood from the following equation:

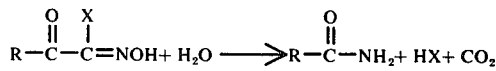

Water, if present in amounts greater than that provided for above, particularly when higher reaction temperatures are employed, substantially diminishes the yield of desired alkylamide product. Also, while the reaction is autocatalytic, the method can also be undertaken with the additional presence of catalytic amounts of a mineral acid hydrochloric acid, sulfuric acid, nitric acid or phosphoric acid to shorten the reaction time.

Specific examples of alkylamides prepared according to the inventive method include acetamide, propanamide, butanamide, pentanamide, hexanamide, heptanamide, octanamide, nonanamide, undecanamide, tridecanamide, tetradecanamide, pentadecanamide and eicosanamide.

At the completion of the reaction, the desired alkylamide can be recovered by cooling the reaction mixture to about 30° C. and lower, suitably 0° to 10° C., and isolating the resulting solid by filtration. An additional benefit derived from employing the oxygenated polar organic solvent is that recovery of the alkylamide is facilitated and obviates the need for extensive purification procedures, such as a plurality of extractions and recrystallizations. Alternatively, the reaction mixture after cooling to below about 60° C. can be contacted with iced water and the resulting alkylamide precipitate recovered as for example, by filtration. Likewise, the hydrogen halide, such as hydrogen chloride, and the solvent can be recovered by distilling the filtrate. The coproduct, carbon dioxide can be recovered, if desired, in the course of the reaction or at the completion thereof by scrubbing the exit gas with an amine base, such as at room temperature and thereafter thermally decomposing the amine-carbon dioxide complex.

The alkylamides prepared according to the instant method are useful as fuel and lubricant additives as in tractor differential hydraulic fluid and automatic transmission fluids, foam stabilizers and synthetic detergents, ore flotation agents, solvents for waxes, dye solubilizers, plasticizers for polymers, surfactants, dispersants or diluents for reactions and in the production of carbon paper, rubber and wax paper, as well as intermediates in the preparation of fabric water repellants. The alkylamides may be hydrolyzed, dehydrated or hydrogenated to form their corresponding acids, nitriles and amines useful in soaps, cosmetics and fabric softeners.

In order to more fully illustrate the nature of our invention and the manner of practicing the same, the following examples are presented.

EXAMPLE I

To a solution composed of 250 milliliters of concentrated HCl (7.1 moles) in 750 milliliters of acetic acid (13 moles) heated to 95° C., there was introduced 100 grams of 1-nitro-2-hexadecanone (0.35 mole). The resulting clear solution was maintained at 95° to 104° C. for 100 minutes. The mixture was thereafter allowed to cool to about 25° C. and crystallized solids weighing 75.5 grams after drying were recovered. The filtrate was further cooled to 0° C. for 1 hour and a second crop of crystallized solids weighing 14.2 grams was collected. Thereafter the filtrate was poured into 150 milliliters of water and a third crop of crystallized product weighing 9.68 grams was collected. A combined yield of 94 percent of theoretical was recovered and this product was identified as n-pentadecanoylhydroximyl chloride by infrared, proton nuclear magnetic resonance and elemental analysis.

A solution composed of 2.2 grams (0.007 mole) of n-pentadecanoylhydroximyl chloride and 100 milliliters (1.75 mole) of glacial acetic acid containing 0.009 mole of water was heated for 25 hours at 118° C. Thereafter the solution was poured into 100 milliliters of ice water. The resulting solids were collected, dried and weighed 1.45 grams (yield 85 percent). The product was identified as pentadecanamide by infrared analysis. No pentadecanoylhydroximyl chloride was detected in the product and only a trace amount of pentadecanoic acid.

EXAMPLE II

A solution composed of 1.0 gram (0.003 mole) of n-pentadecanoylhydroximyl chloride and 3 milliliters of dimethylsulfoxide containing about two weight percent water was heated up to 110° C. over a period of two hours. Thereafter, the solution was poured into four grams of ice water and stirred for several hours. The resulting solids were collected, dried and weighed 0.43 gram (60% yield). The solid product was identified by infrared analysis to be mainly pentadecanamide.

We claim:

1. A method of preparing an alkylamide which comprises heating an acylhydroximyl halide with an oxygenated polar organic solvent at a temperature of from about 70° to 190° C.

2. A method according to claim 1 wherein said heating is at a temperature of about 90° C. to 140° C.

3. A method according to claim 1 wherein said heating is at a temperature of about 110° to 140° C.

4. A method according to claim 1 wherein the mole ratio of said halide to said solvent is between about 1:1 and 1:100.

5. A method according to claim 1 wherein the mole ratio of said halide to said solvent is between 1:4 and 1:40.

6. A method according to claim 1 wherein said acylhydroximyl halide corresponds to the formula:

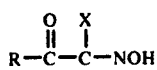

where R is an alkyl group of from 1 to 50 carbon atoms and where X is Cl, Br, I or F.

7. A method according to claim 6 where X is Cl.

8. A method according to claim 6 where R is 3 to 40 carbon atoms.

9. A method according to claim 6 where R is 5 to 30 carbon atoms.

10. A method according to claim 1 wherein said acylhydroximyl halide is pentadecanoylhydroximyl chloride.

11. A method according to claim 1 wherein said acylhydroximyl halide is heptadecanoylhydroximyl chloride.

12. A method according to claim 1 wherein said acylhydroximyl halide is pentadecanoylhydroximyl bromide.

13. A method according to claim 1 wherein said acylhydroximyl halide is pentadecanoylhydroximyl iodide.

14. A method according to claim 1 wherein said acylhydroximyl halide is pentadecanoylhydroximyl fluoride.

15. A method according to claim 1 wherein said solvent is an alkanoic acid, an alkylformamide, an alkylacetamide, an alkylsulfoxide, an alkylurea, an alkylphosphoramide, an alkylpyrrolidinone, an aldehyde, a ketone or an ether.

16. A method according to claim 1 wherein said solvent is an alkanoic acid having 1 to 16 carbon atoms.

17. A method according to claim 1 wherein said solvent is an alkanoic acid of 2 to 6 carbon atoms.

18. A method according to claim 1 wherein said solvent is acetic acid.

19. A method according to claim 1 wherein said solvent is dimethylsulfoxide.

20. A method according to claim 1 wherein said heating is conducted in the presence of from about one to below about five moles of water per mole of said halide.

21. A method according to claim 1 wherein said heating is conducted in the presence of catalytic amounts of a mineral acid.

22. A method according to claim 1 wherein said alkylamide is pentadecanamide.

23. A method according to claim 1 wherein said alkylamide is acetamide.

* * * * *